(12) United States Patent
Gennari et al.

(10) Patent No.: US 11,684,588 B2
(45) Date of Patent: Jun. 27, 2023

(54) MULTILAYER COMPOSITE MATERIAL

(71) Applicant: FIDIA FARMACEUTICI S.P.A., Abano Terme (IT)

(72) Inventors: Giovanni Gennari, Abano Terme (IT); Monica Campisi, Abano Terme (IT); Anna Maria Zanellato, Abano Terme (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 16 days.

(21) Appl. No.: 16/975,672

(22) PCT Filed: Feb. 26, 2019

(86) PCT No.: PCT/IB2019/051534
§ 371 (c)(1),
(2) Date: Aug. 25, 2020

(87) PCT Pub. No.: WO2019/162928
PCT Pub. Date: Aug. 29, 2019

(65) Prior Publication Data
US 2020/0405656 A1   Dec. 31, 2020

(30) Foreign Application Priority Data

Feb. 26, 2018   (IT) .................. 102018000003034
Dec. 27, 2018   (IT) .................. 102018000021112

(51) Int. Cl.
| | | |
|---|---|---|
| *A61K 9/70* | (2006.01) |
| *A61F 13/00* | (2006.01) |
| *A61K 33/38* | (2006.01) |
| *A61K 38/39* | (2006.01) |
| *A61K 47/26* | (2006.01) |
| *A61K 47/34* | (2017.01) |
| *A61K 47/36* | (2006.01) |

(52) U.S. Cl.
CPC ...... *A61K 9/7092* (2013.01); *A61F 13/00063* (2013.01); *A61K 33/38* (2013.01); *A61K 38/39* (2013.01); *A61K 47/26* (2013.01); *A61K 47/34* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 5,800,372 A | 9/1998 | Bell et al. | |
| 10,328,063 B2 * | 6/2019 | Jagannath | ............ A61K 31/439 |
| 2008/0171958 A1 * | 7/2008 | Gundersen | ............ A61F 13/022 |
| | | | 602/56 |

FOREIGN PATENT DOCUMENTS

| | | | | |
|---|---|---|---|---|
| EP | 3100748 A1 * | 12/2016 | ....... A61F 13/00017 |
| WO | WO 2006/089551 A1 | 8/2006 | |

OTHER PUBLICATIONS

Passi (Why low molecular weight HA in wound healing? May 5, 2017). (Year: 2017).*
International Search Report for PCT/IB2019/051534 (PCT/ISA/210) dated Jun. 25, 2019.
Written Opinion of the International Searching Authority for PCT/IB2019/051534 (PCT/ISA/237) dated Jun. 25, 2019.

* cited by examiner

*Primary Examiner* — Melissa S Mercier
(74) *Attorney, Agent, or Firm* — Birch, Stewart, Kolasch & Birch, LLP

(57) ABSTRACT

The present invention relates to a multilayer composite material for the treatment of wounds and lesions and to a dressing comprising said multilayer material.

5 Claims, No Drawings

MULTILAYER COMPOSITE MATERIAL

The present invention relates to a multilayer composite material for the treatment of wounds and injuries.

The treatment of wounds and lesions of the skin, and, optionally, of the underlying tissues, to obtain cicatrization and healing, preferably with minimal aesthetic and functional consequences for the subject involved, is still a deeply felt need, to which it is not always possible to give a satisfactory answer either in the field of personal care or in hospitals.

In particular, dressings are available in the form of gauzes, compresses, plasters or the like, impregnated or soaked in substances having a healing action, possibly associated with antibacterials and/or antiseptics. Gauzes impregnated with fatty substances or hydrocolloids, for example, are known in the state of the art, which act in a non-specific way, or with substances having an actual healing and repairing action, such as natural extracts or hyaluronic acid (HA). The latter in particular has been widely used for a long time in the treatment of wounds, ulcers and skin lesions of various origins, superficial or deep, thanks to its well-known properties on the regeneration of tissues.

It has been found, however, that dressings comprising a supporting fabric, commonly used for the treatment of wounds and injuries, have the disadvantage that they can adhere to the biological tissues of the wound being repaired until they are partially englobed by the same. It should be considered, in fact, that supporting fabrics may be hydrophilic or hydrophobic in nature, depending on the type of dressing to be obtained and the type of lesion to be treated; for example, for an exuding wound, an absorbent hydrophilic supporting fabric, such as a cotton gauze, is preferred. Furthermore, in order to convey the appropriately formulated healing substance, they must have large pores, in which the cicatrizing composition is distributed; it is precisely the pore size that facilitates the colonization of the supporting material by the scar tissue being formed.

This involves, during the dressing-change phase, the removal of portions of the biological tissues present, in particular those in the regeneration phase and the possible consequent reopening of the wound with prolongation of the healing process. Furthermore, it should not be forgotten that this causes severe pain in the patient. In particular, in cases of wounds with exudate and/or in the presence of biological tissues undergoing necrotization (eschar), the removal of parts of the biological tissue that have incorporated the dressing results in severe complications of the healing process, which may lead to scar formation and increase the risk of infection of the site of the original wound and the surrounding area.

A further important disadvantage of the known dressings is due to the fact that, as the healing substance is arranged on a single layer of supporting material, it is released in the lesion very rapidly, not homogeneously and not constantly over time.

Furthermore, fabrics based on natural fibers, such as cotton, commonly used in gauzes, can release debris/residues in the wound, which can complicate the healing process and/or be incorporated in the post-healing biological tissues, with unpleasant aesthetic aspects.

For all of these reasons, the dressings currently available must be replaced, at least ideally, every 6-8 hours, with consequent economic costs and with the need for constant intervention by the subject who has suffered a wound or injury and/or specialized personnel.

The applicant has now surprisingly found that the disadvantages listed above can be overcome.

DESCRIPTION

An object of the present invention relates to a multilayer composite material (CM) comprising at least:

a) a three-dimensional matrix comprising at least:
a first layer i. and a second layer ii. of a fabric comprising, or consisting of a polyester fiber, wherein said first layer i. and said second layer ii. are superimposed and welded together in at least two distinct and separate points, so as to define a space S between the two layers i. and ii. and b) a composition comprising, or consisting of
at least one natural, semi-synthetic or synthetic polymer, possibly mixed together;
possibly one or more pharmacologically and/or biologically active substance, and
at least one excipient suitable for pharmaceutical use,
wherein said composition b) is contained in at least a part of said space S included between the layers i. and ii.

A further object of the present invention relates to a multilayer composite material (CM) as defined above for use in the treatment of a wound, abrasion, cut, ulcer, sore, burn, lesion or laceration of the skin in a subject, wherein said treatment comprises the application of said multilayer composite material on the surface of the wound, abrasion, cut, ulcer, sore, burn, lesion or laceration of the skin and, possibly, of the underlying tissues.

The applicant has therefore surprisingly found that the disadvantages listed above can be overcome by means of a multilayer composite material whose supporting structure is a three-dimensional matrix, consisting of at least two layers of synthetic fabric, fixed together at regular intervals, to form a cage which contains a healing substance, preferably hyaluronic acid, which is released homogenously, uniformly and constantly over time.

The multilayer composite material, object of the present invention, is provided with the following features:

it is soft, flexible, can be cut according to the site of application and is therefore perfectly adaptable to the bed of the wound;

it allows a uniform and homogeneous distribution of the cicatrizing composition, preferably HA, and therefore a constant release over time;

it remains firmly fixed on the wound;

it can be easily and painlessly removed, and without the undesired removal of newly formed healing tissue;

it does not release debris/residues in the wound;

it can be sterilized with gamma or beta rays;

it can be replaced every 24, 48 or 72 hours.

The combination of these characteristics makes it effective in promoting the healing of wounds on which it is applied and absolutely innovative compared to what is currently available.

Unless otherwise indicated, within the scope of the present invention, the percentages and quantities of a component in a mixture should refer to the weight of said component with respect to the total weight of the mixture.

Unless otherwise specified, within the scope of the present invention, the indication that a composition "comprises" one or more components or substances means that other components or substances may be present in addition to that, or those, specifically indicated.

Unless otherwise specified, within the scope of the present invention, a range of values indicated for an amount, for example the weight content of a component, includes the lower limit and the upper limit of the range. For example, if the weight or volume content of a component A is indicated as "from X to Y", wherein X and Y are numerical values, A can be X or Y or any of the intermediate values.

In the context of the present invention, the term "multilayer composite material (CM)" indicates the combination of at least two layers (i. and ii.) of fabric comprising at least one polyester and of the composition b) which is contained inside the space between said layers i. and ii.

It is understood that said multilayer composite material (CM) may constitute, or form part of, a dressing suitable for the treatment of a wound, injury, laceration, ulcer, burn and the like, which is suitable for protecting and promoting the healing of said wound, injury, laceration, ulcer, burn and the like. In particular, the multilayer composite material (CM) of the present invention can be used in the preparation of an advanced dressing, i.e. comprising coating materials with biocompatibility characteristics and at least one active material, i.e. capable of playing an active role in tissue repair and, at times, modifying the cellular matrix.

By way of non-limiting example, the composite material (CM) or the dressing comprising said material according to the present invention can be in the form of a gauze, a compress, a plaster or the like. The cicatrizing composition b) contained in the three-dimensional matrix a) can be in different pharmaceutical forms also according to the component/s forming said composition. Creams, ointments, emulsions, gels and hydrogels, powders, water-based and non-water-based solutions, suspensions, etc., should therefore be considered as being possible pharmaceutical forms of the composition b).

The multilayer composite material (CM) according to the present invention can be used in human subjects or for veterinary use, for example, but without limitation, in pets such as dogs or cats, or in other mammals. The multilayer composite material (CM) according to the present invention is preferably for use in human beings.

In the context of the present invention, "wound", "injury", "laceration", "ulcer", "burn" and similar terms, refer to any interruption of the integrity of the skin such as, without limitation, those due to a traumatic event, surgery, pathologies or disorders of various kinds (e.g. diabetic or vascular ulcers), to sores, for example from decubitus, to a tear or bruise, with or without the production of exudates and/or the effusion of body fluids such as blood.

In the composition b) of the multilayer composite material (CM) according to the present invention, comprising or consisting of at least one natural, semi-synthetic or synthetic polymer, possibly mixed together;

possibly one or more pharmacologically and/or biologically active substances, and at least one excipient suitable for pharmaceutical use, wherein said composition b) is contained in at least a part of said space S included between the layers i. and ii., the natural or semi-synthetic polymers are preferably selected from polysaccharides, proteins, polypeptides or polynucleotides; the synthetic polymers are preferably selected from polyacrylic acid; polyacrylates and relative derivatives, such as pHEMA [poly-2-hydroxyethyl-methacrylate]; polyaspartamide; poly(ethyleneglycol) (PEG); polyvinyl-pyrrolidone; polylactic acid, poly(lactic-glycolic) acid such as poly-lactic-co-glycolic acid (PLGA), polyglycolic acid (PGA), polycaprolactone; polyanhydrides; polyorthoesters; polyphosphoesters; polyphosphazenes; polycyanoacrylic derivatives; poly(N-isopropylacrylamide); polylysine; polyhistidine; polyamidoamine; polyglutamic acid; polysiloxanes; polyurethanes; polytetrafluoroethylene (PTFE); even more preferably, the synthetic polymers are polyurethanes.

The polysaccharides are preferably selected from:

glycosaminoglycans: more preferably hyaluronic acid and/or derivatives thereof such as salts, esters, amides and sulfated hyaluronic acid; hybrid complexes of high- and low-molecular-weight hyaluronic acid (as described in WO2012/032151); chondroitin, chondroitin sulfate, dermatan sulfate, keratansulfate, heparan sulfate, heparin and heparinoids;

chitin, chitosan and its derivatives: more preferably chitosan derivatized with lactose (as described in WO2007/135116 and WO2017/211776);

pectin or pectinic acid;

galactans: more preferably agar and agarose;

alginates: more preferably alginic acid;

glucans: more preferably dextran, dextrin, trehalose, maltose, starch, cellulose and its derivatives, and even more preferably hydroxyethylcellulose, carboxymethylcellulose, hydroxymethylcellulose and cellulose acetate;

natural gums, xanthan, gellan;

fructans: preferably inulin;

polymannans;

carrageenan.

The proteins or polypeptides are preferably selected from:

collagen, co-precipitates of collagen and glycosaminoglycans, gelatin, elastin, fibrin, fibrinogen, keratin, silk, silk fibroin alone or in combination with sericin, silk sericin.

The most preferred polysaccharides are the sodium salt of hyaluronic acid with a molecular weight ranging from 150 to 2,000 kDa, the above-mentioned hybrid complexes in which the high-molecular-weight hyaluronic acid ranges from 1,100 to 1,400 kDa and the low-molecular-weight hyaluronic acid ranges from 80 to 100 kDa, and chitosan derivatized with lactose, whereas even more preferred proteins are collagen and silk proteins.

The pharmacologically and/or biologically active substances possibly present in the composition b) of the multilayer composite material (CM) according to the present invention, can be medical extracts of a natural or synthetic origin; drugs for topical use such as non-steroidal anti-inflammatory drugs (NSAIDs); various kinds of steroids; antibacterials/antibiotics, preferably silver sulfadiazine; cytostatics, preferably metallic silver; growth factors; fibrinolytic and antiedematous substances; proteolytic enzymes, preferably collagenases; hyaluronidase; anticoagulants.

The composition b) preferably comprises:

sodium salt of hyaluronic acid (HA), prepared from hyaluronic acid having a weight average molecular weight ranging from 150 to 2,000 kDa, preferably from 150 to 500 kDa, even more preferably from 150 to 250 kDa, as such, or in association with another polysaccharide, preferably with chitosan derivatized with lactose, possibly a protein selected from silk fibroin and collagen, possibly pharmacologically and/or biologically active substances, preferably in combination with silver sulfadiazine or metallic silver.

In a different embodiment of the present invention, the composition b) preferably comprises:

sodium salt of hyaluronic acid (HA), prepared from hyaluronic acid having a weight average molecular weight ranging from 150 to 250 kDa, or hybrid complexes of hyaluronic acid having a high and low molecular weight or a mixture thereof, possibly a protein selected from silk fibroin and collagen, possibly in association with pharmacologically and/or biologically active substances, preferably in combination with silver sulfadiazine or metallic silver.

A preferred medical extract of a natural origin is the extract of Triticum vulgare, which is used in the composite multilayer material of the present invention and can be obtained by the methods commonly used for the extraction of active ingredients from plant raw materials and known to persons skilled in the field.

The composite multilayer material of the present invention can, as a non-limiting example, comprise a composition comprising aqueous extract of Triticum vulgare, for example having a dry residue of about 200 mg/100 ml, and optionally also comprising phenoxyethanol.

In the context of the present invention, "hyaluronic acid" (hereinafter also "HA") refers to a hetero-polysaccharide composed of alternating residues of D-glucuronic acid and N-acetyl-D-glucosamine, with a linear chain, with a molecular weight which can range from 400 to $3 \times 10^6$ Dalton (Da), depending on the extraction source or preparation method used. HA is ubiquitously present and plays an important role in the biological organism, especially as a mechanical support of the cells of many tissues such as the skin, tendons, muscles and cartilage.

It is also known that HA, through its membrane receptor CD44, modulates many different processes relating to the physiology and biology of cells such as, for example, proliferation, migration, cell differentiation and angiogenesis, and carries out further important functions such as the hydration of tissues and the lubrication of the joints. It has been shown that HA is determinant in the tissue repair process both from the structural point of view (in the organization of the extracellular matrix and in the regulation of its hydration) and also as a stimulating substance of a wide range of processes in which it intervenes directly and indirectly (formation of coagulation, phagocytic activity, fibroblast proliferation, neovascularization, re-epithelialization, etc.) (Weigel P. et al., *J Theoretical Biol,* 1986: 219-234; Abatangelo G. et al., *J Surg Res,* 1983, 35: 410-416; Goa K. et al., *Drugs,* 1994, 47: 536-566).

The combination of these widely recognized properties has long been exploited in the preparation of dressings used in the treatment of wounds, ulcers and skin lesions of various origins, superficial or deep.

The HA used in the present invention can derive from any source, for example, from rooster combs (EP138572), from fermentation (from *Streptococcus equi* or *zooepidemicus,* EP0716688), or from biosynthesis (from *Bacillus,* EP2614088 A1, EP2614087 A1), and be purified according to different techniques (WO2018/020458 A1, IT102017000081449). The weight average molecular weight (MW) of the polymer for the applications described herein can range from 400 to $3 \times 10^6$ Da, preferably from 100,000 to $2 \times 10^6$ Da, more preferably from 150 to 2,000 kDa, even more preferably from 150 to 500 kDa or from 150 to 250 kDa. For the sake of brevity, the latter is generally referred to as "HA with average weight MW 200 kDa".

In the context of the present invention, average molecular weight of HA refers to the weight average MW calculated with the "intrinsic viscosity" method (Terbojevich et al., *Carbohydr Res,* 1986, 363-377).

It is understood that the MW is that of the starting hyaluronic acid before preparing the finished product, i.e. at the moment of preparation of the impregnating composition.

In a preferred embodiment of the present invention, in the multilayer composite material (CM), the hyaluronic acid in the composition b) has an average molecular weight ranging from 150 kDa to 500 kDa, more preferably from 150 to 250 kDa. The inventors have surprisingly found that the multilayer composite material (CM) according to the present invention allows a dressing of wounds and lesions of the skin in general, which is effective, easy to use and practically free of the disadvantages of the known dressings described above.

The multilayer composite material (CM) according to the present invention comprises a three-dimensional matrix a), which is composed of at least two layers (i. and ii) of polyester fabric, preferably polyethylene terephthalate (PET), preferably monofilament, held together by two or more joints or welding points, carried out, for example, by ultrasound, at regular intervals. The structure of the multilayer composite material (CM) according to the present invention is similar to that of a quilted fabric, in which the two layers i. and ii. are superimposed through the most extended surfaces, like the pages of a book. A cage is then formed which entraps the healing substance inside, specifically HA, and which releases it gradually, homogeneously, continuously and constantly through the pores of the fabric, wherein fabric specifically refers to a thin and flexible product with a flat surface, produced by an interweaving of threads perpendicular to each other.

The weave, that is the combination of weft and warp, of the single layer of fabric is thick, and consequently the pores between one mesh and the other have very reduced dimensions. As known to skilled persons in the field, the weave of a fabric is modulated, with the same thread size, by varying the number of meshes which, horizontally and vertically, with respect to a reference unit, constitute the fabric. In this specific case, the number of meshes in 1 cm of fabric varies, vertically, from 10 to 15, and preferably from 11 to 12, and horizontally, ranges from 10 to 17, and preferably from 11 to 15. This thick weave and, therefore, extremely small pores, on the one hand ensure flexibility of the material and, on the other, prevent the fabric itself from integrating, even minimally, with the wound on which it is applied.

It should be pointed out that the layers of fabric i. and ii. to be coupled to constitute the three-dimensional matrix a) must be identical, i.e. having the same number of meshes horizontally and vertically respectively.

Furthermore, the matrix a) comprising, or consisting of, polyester fabric, preferably PET, preferably monofilament, does not release fibers in biological tissues, therefore the risk of contamination and the presence of gauze residues in the biological tissues after dressing is minimized.

It is understood that the multilayer composite material (CM) according to the present invention can also comprise other layers of fabric or other components in addition to the layers i. and ii., as described above.

The matrix a) obtained by welding at least two layers of fabric comprising polyester, preferably PET, as described above, can be impregnated with an aqueous base composition comprising at least hyaluronic acid and one or more excipients suitable for pharmaceutical use. Said composition fills, at least in part, the space S between the two layers i. and ii., producing the multilayer composite material (CM) according to the invention. Said composition is preferably distributed uniformly throughout the space S defined by the two layers i. and ii. of the matrix a). Said composition can also be present, at least in part, on the surfaces of the layers i. and ii. that are external to the intermediate space S.

In other words, the multilayer composite material (CM) according to the present invention comprises a three-dimensional matrix that forms a cage which entraps the HA composition, releasing it progressively.

Non-limiting examples of the excipients which can be used in said composition comprising hyaluronic acid are all excipients suitable for the production of pharmaceutical formulations, including, without limitation, polyethylene glycol (PEG) and polyols, such as glycerol.

There are numerous advantages of the present invention. The multilayer composite material (CM) according to the present invention has, among others, the following advantages.

The multi-layer composite material (CM) is soft, flexible, can be easily cut, for example with scissors, and is therefore perfectly adaptable to the bed of the wound.

The multilayer composite material (CM) allows uniform and homogeneous distribution of the HA composition, and therefore a uniform and homogeneous release of the same.

The multilayer composite material (CM) remains firmly fixed on the wound even without any adhesive, even if the presence of adhesive layers is not excluded from the scope of the present invention.

The multilayer composite material (CM) can be easily and painlessly removed, as the very small pores due to the thick weave and hydrophobic nature of the polyester, also prevent surface integration with the eschar, especially in the case of exuding wounds, and therefore newly formed scarring tissue is not torn away from the wound at the moment of removal.

The multilayer composite material (CM) does not release debris/residues, such as fiber fragments, in the wound.

The multilayer composite material (CM) can be sterilized with gamma or beta rays. For all these characteristics, the multilayer composite material (CM) according to the present invention can be replaced every 24, 48 or 72 hours, instead of every 8 hours as necessary for wound-dressing products currently on the market.

When the composition b) comprises only synthetic polymers such as polyurethanes, the multilayer composite material (CM) can however be particularly advantageous, as it can absorb the exudates with particular effectiveness.

In a preferred embodiment, in the multilayer composite material (CM) according to the present invention, the composition b) further comprises metallic silver or at least a silver salt, preferably silver sulfadiazine.

In the context of the present invention, the term "silver sulfadiazine" refers to the monoargentic salt (Ag (I)) of sulfadiazine, CAS No. 22199-08-2. It is intended that silver sulfadiazine derivatives and complexes can also form part of the composition of the invention.

In the context of the present invention, the term "metallic silver" refers to all forms of silver in oxidation state 0 known to skilled persons in the field of pharmaceutical formulations, including, without limitation, micronized and colloidal silver.

In a preferred embodiment of the invention, in the multilayer composite material (CM), the fabric of the layer i. and/or of the layer ii. is a monofilament fabric.

In a preferred embodiment of the invention, in the multilayer composite material (CM), the fabric of the layer i. and/or of the layer ii. comprises, or consists of, polyester, more preferably at least one of polyethylene terephthalate (PET), a natural polyester, such as a polyhydroxyalkanoate (PHA), e.g. polyhydroxybutyrate (PHB), even more preferably PET (polyethylene terephthalate).

In a preferred embodiment of the invention, in the multilayer composite material (CM), the fabric of the layer i. and/or of the layer ii. contains from 10 to 15 meshes, preferably from 11 to 12, vertically and from 10 to 17 mesh, preferably from 11 to 15, horizontally.

In a preferred embodiment of the invention, the multilayer composite material (CM) has a thickness ranging from 0.2 to 2 mm, even more preferably from 0.5 to 1 mm.

The dimensions of the dressing are variable depending on the type of wound or injury to be treated. As a non-limiting example, the multilayer composite material (CM) can have dimensions varying from 5×5 cm. to 30×30 cm, preferably 10×10 cm.

The welding between the two layers i. and ii, and, if present, between other layers of the three-dimensional matrix a) can be carried out, as a non-limiting example, by means of ultrasounds. Said welding is preferably effected so as to produce punching at a distance that can vary from 10 to 20 mm, more preferably from 15 to 16 mm, with a regular or irregular pattern.

In the multilayer composite material (CM) according to the present invention, the concentration of HA in the impregnation composition, expressed as w/w with respect to the impregnation composition, ranges from 0.01 to 1%, preferably from 0.02 to 0.5%, even more preferably from 0.03% to 0.2%.

The amount of HA in the final dressing can vary according to the size of the dressing. In a dressing having dimensions of 10×10 cm, for example, the HA varies from 0.4 to 40 mg, preferably from 0.8 to 20 mg, even more preferably from 1.2 to 8 mg.

The concentration of silver sulfadiazine, expressed as weight/weight with respect to the impregnating composition, preferably ranges from 0.1 to 3%, and is more preferably equal to 1%.

In addition to HA and, when present, silver sulfadiazine, at the concentration ranges mentioned above, the impregnating composition can also comprise as excipients, glycerol in variable amounts ranging from 10 to 30%, preferably equal to 25%, PEG 4000 in variable amounts ranging from 30 to 70%, preferably equal to 50%, and water for the remaining part; the quantities are expressed as weight with respect to the weight of the final composition.

In an embodiment, the present invention also relates to a dressing consisting of or comprising a) a three-dimensional matrix comprising at least a first layer i. end a second layer ii. of fabric including, or consisting of a PET fiber, wherein said first layer i. and said second layer ii. are superimposed and welded together in at least two different and separated points, so as to define a space S between the two layers i. and ii. and b) a composition comprising, or consisting of hyaluronic acid, and at least one excipient suitable for pharmaceutical use, and possibly further comprising silver sulfadiazine, wherein said composition b) is contained in at least a part of said space S between the layers i. and ii.

wherein said dressing has dimension of about 9×9 cm and contains 4.1±0.5 g of composition b) prepared starting from hyaluronic acid having a weight average molecular weight ranging from 150 to 250 kDa, the total content of HA in the dressing being equal to 2 mg and the total content of silver sulfadiazine in the dressing, when present, being equal to 40 mg.

In an embodiment, the present invention also relates to a dressing consisting of or comprising the multilayer composite material (CM), wherein said dressing has dimensions of about 9×9 cm and contains 4.1±0.5 g of composition b), prepared starting from hyaluronic acid having a weight average molecular weight ranging from 150 to 250 kDa, the total content of HA in the dressing being equal to 2 mg.

The silver sulfadiazine, when present, is preferably 1%, therefore each dressing contains about 40 mg of silver sulfadiazine. In a preferred embodiment, the fabric of the layer i. and ii. consists of monofilament polyethylene terephthalate and preferably contains from 11 to 12 meshes per centimetre vertically and preferably from 11 to 15 meshes per centimetre horizontally. The layers of fabric forming the three-dimensional matrix a) are welded by means of ultrasounds with punching at a distance ranging from 15 to 16 mm. An object of the present invention relates to the multilayer composite material (CM) as described above, or a dressing comprising said composite material (CM), for the use in the treatment of a wound, abrasion, cut, ulcer, sore, burn, lesion or laceration of the skin in a subject, wherein said treatment includes the application of said multilayer composite material on the surface of the wound, abrasion, cut, lesion or laceration of the skin and, possibly, of the underlying tissues.

In a preferred embodiment, in the multilayer composite material (CM) for the use described above, the composition b) also comprises silver sulfadiazine.

An object of the present invention also relates to a method for the treatment of a wound, abrasion, cut, ulcer, sore, burn, lesion or laceration of the skin in a subject which comprises the application of the multilayer composite material (CM) as described above, or the application of a dressing comprising said composite material (CM) on the part of the body of the subject affected by the wound, abrasion, cut, lesion or laceration of the skin.

The invention claimed is:

1. A dressing comprising:
   a) a three-dimensional matrix comprising at least a first layer and a second layer of a fabric consisting of a polyethylene terephthalate (PET) fiber, wherein said first layer and said second layer are superimposed and welded together in at least two distinct and separate points, so as to define a space S between the first layer and the second layer; and
   b) a composition consisting of hyaluronic acid and at least one excipient suitable for pharmaceutical use, wherein said composition b) is contained in at least a part of the space S between the first layer and the second layer;
   wherein said dressing has dimensions of about 9×9 cm and contains 4.1±0.5 g of composition b) prepared starting from hyaluronic acid having a weight average molecular weight ranging from 150 to 250 kDa, wherein the total content of hyaluronic acid (HA) in the dressing is equal to 2 mg;
   wherein said composition b) is present at least in part on the surfaces of the first layer and second layer that are external to the intermediate space S; and
   wherein the fabric of the first layer and of the second layer is a monofilament fabric.

2. The dressing according to claim 1, wherein the fabric of the first layer and/or of the second layer contains from 10 to 15 meshes, vertically, and from 10 to 17 meshes horizontally.

3. The dressing according to claim 1, wherein the fabric of the first layer and/or of the second layer are welded by means of points obtained by welding so as to obtain points at a distance ranging from 10 to 20 mm from one another.

4. A method of treating a wound, abrasion, cut, ulcer, sore, burn, lesion or laceration of the skin in a subject, which comprises applying the dressing according to claim 1 to the surface of the wound, abrasion, cut, ulcer, sore, burn, lesion or laceration of the skin and, optionally, of the underlying tissues.

5. A dressing comprising:
   a) a three-dimensional matrix comprising at least a first layer and a second layer of a fabric consisting of a polyethylene terephthalate (PET) fiber, wherein said first layer and said second layer are superimposed and welded together in at least two distinct and separate points, so as to define a space S between the first layer and the second layer; and
   b) a composition consisting of hyaluronic acid, silver sulfadiazine, and at least one excipient suitable for pharmaceutical use, wherein said composition b) is contained in at least a part of the space S between the first and the second layer;
   wherein said dressing has dimensions of about 9×9 cm and contains 4.1±0.5 g of composition b) prepared starting from hyaluronic acid having a weight average molecular weight ranging from 150 to 250 kDa, wherein the total content of hyaluronic acid (HA) in the dressing is equal to 2 mg and the total content of silver sulfadiazine in the dressing is equal to 40 mg;
   wherein said composition b) is present at least in part on the surfaces of the first layer and second layer that are external to the intermediate space S; and
   wherein the fabric of the first layer and of the second layer is a monofilament fabric.

* * * * *